United States Patent
Iikubo et al.

(10) Patent No.: US 7,412,776 B2
(45) Date of Patent: Aug. 19, 2008

(54) SENSOR HOLDING APPARATUS

(75) Inventors: Katsushi Iikubo, Nagoya (JP); Hidehito Sasaki, Nagoya (JP); Hidenori Suzuki, Nagoya (JP); Hiromasa Tsukahara, Nagoya (JP); Chikao Harada, Nagoya (JP); Hitoshi Hirano, Nagoya (JP); Hiroshi Masuda, Nagoya (JP)

(73) Assignee: Unex Corporation, Nagoya (JP)

( * ) Notice: Subject to any disclaimer, the term of this patent is extended or adjusted under 35 U.S.C. 154(b) by 38 days.

(21) Appl. No.: 11/507,545

(22) Filed: Aug. 22, 2006

(65) Prior Publication Data

US 2007/0044336 A1 Mar. 1, 2007

(30) Foreign Application Priority Data

Aug. 26, 2005 (JP) .............................. 2005-245169

(51) Int. Cl.
  *G01B 5/004* (2006.01)
  *E04G 3/00* (2006.01)
(52) U.S. Cl. ...................... 33/503; 33/613; 248/280.11; 248/284.1
(58) Field of Classification Search .................. 33/503, 33/569, 572, 573, 613, 645; 248/123.2, 280.11, 248/284.1, 292.11, 292.13, 325, 585
See application file for complete search history.

(56) References Cited

U.S. PATENT DOCUMENTS 4,712,313 A * 12/1987 Gettleman ................ 248/284.1
4,924,598 A * 5/1990 Gruhler ........................ 33/503
5,170,975 A * 12/1992 Chadwick ................ 248/284.1
5,538,214 A * 7/1996 Sinila ...................... 248/284.1

(Continued)

FOREIGN PATENT DOCUMENTS

JP         A 1-155828         6/1989

(Continued)

*Primary Examiner*—G. Bradley Bennett
(74) *Attorney, Agent, or Firm*—Oliff & Berridge, PLC

(57) ABSTRACT

An apparatus for holding a sensor such that the sensor touches an object at an arbitrary position in a three-dimensional space, the apparatus including a base member; a rotatable member which is rotatable relative to the base member about a vertical axis line; a first link device including a first stationary link, a first movable link, and two first pivotable links which are pivotably connected to the first stationary link and the first movable link, such that the first stationary link, the first movable link, and the two first pivotable links cooperate with each other to define a quadrilateral, wherein the first stationary link is fixed to the rotatable member such that the first movable link is movable in a plane containing the axis line; a second link device including two second pivotable links, and a second stationary link and a second movable link which are pivotably connected to the two second pivotable links, such that the two second pivotable links, the second stationary link, and the second movable link cooperate with each other to define a quadrilateral, wherein the second stationary link is fixed to the first movable link such that the second movable link is movable in the plane containing the axis line, and wherein the second movable link supports the sensor; a first biasing device which produces a thrust having a directional component resisting a load applied to the first movable link; and a second biasing device which produces a thrust having a directional component resisting a load applied to the second movable link.

9 Claims, 4 Drawing Sheets

U.S. PATENT DOCUMENTS

| | | | |
|---|---|---|---|
| 6,640,458 B2 * | 11/2003 | Sawdon | 33/503 |
| 6,732,988 B2 * | 5/2004 | Ihalainen et al. | 248/280.11 |
| 2003/0075658 A1 * | 4/2003 | Beissel et al. | 248/284.1 |
| 2005/0166413 A1 * | 8/2005 | Crampton | 33/503 |
| 2007/0256311 A1 * | 11/2007 | Ferrari | 33/503 |

FOREIGN PATENT DOCUMENTS

JP     A 2000-254105     9/2000

* cited by examiner

SENSOR HOLDING APPARATUS

The present application is based on Japanese Patent Application No. 2005-245169 filed on Aug. 26, 2005, the contents of which are incorporated herein by reference.

BACKGROUND OF THE INVENTION

1. Field of the Invention

The present invention relates to a sensor holding apparatus that holds a sensor such that the sensor touches an object at a predetermined position in a three-dimensional space.

2. Related Art Statement

There is a need to hold, at an appropriate position, a sensor such that the sensor lightly contacts, i.e., touches an object. The sensor is, e.g., an ultrasonic sensor that touches skin and detects an image under the skin; a photoelectric-pulse-wave sensor that touches skin and detects a photoelectric pulse wave; or a pressure-pulse-wave sensor that touches skin right above an artery and detects a pressure pulse wave from the artery.

To meet the above-identified need, Patent Document 1 (Japanese Patent Application Publication No. 2000-254105) proposes a sensor holding apparatus that holds a sensor such that the sensor contacts a specific portion of skin of a living being. However, in this sensor holding apparatus, a belt wound around an arm of the living being is utilized to press the sensor against the skin. Therefore, this apparatus suffers the disadvantage that the contact pressure is too high and the cross-sectional shape of the underlying blood vessel is deformed. In addition, this apparatus suffers another disadvantage that the sensor cannot easily be moved on the skin surface to seek a target tissue.

Meanwhile, Patent Document 2 (Japanese Patent Application Publication No. 1(1989)-155828) proposes a sensor holding apparatus that holds, without using a belt, a sensor such that the sensor is positioned relative to a specific portion of skin of a living being, without being contacted with the skin. Therefore, this sensor holding apparatus can be used to hold the sensor such that the sensor lightly contacts, i.e., touches the skin.

SUMMARY OF THE INVENTION

However, in the sensor holding apparatus disclosed by Patent Document 2, though the sensor can be held such that the sensor touches the skin, an arm holding the sensor can be moved in one direction only and accordingly the sensor cannot easily be moved on the skin surface to seek a target tissue.

It is therefore an object of the present invention to provide a sensor holding apparatus that can hold a sensor such that the sensor touches an outer surface of an object and such that the sensor can easily be moved on the outer surface of the object so as to seek a target portion of the object.

The above object has been achieved by the present invention. According to a first mode of the present invention, there is provided an apparatus for holding a sensor such that the sensor touches an object at an arbitrary position in a three-dimensional space, the apparatus comprising a base member; a rotatable member which is rotatable relative to the base member about a vertical axis line; a first link device including a first stationary link, a first movable link, and two first pivotable links which are pivotably connected to opposite end portions of the first stationary link and opposite end portions of the first movable link, such that the first stationary link, the first movable link, and the two first pivotable links cooperate with each other to define a quadrilateral, wherein the first stationary link is fixed to the rotatable member such that the first movable link is movable in a plane containing the axis line; a second link device including two second pivotable links, and a second stationary link and a second movable link which are pivotably connected to opposite end portions of one of the two second pivotable links and opposite end portions of an other of the two second pivotable links, such that the two second pivotable links, the second stationary link, and the second movable link cooperate with each other to define a quadrilateral, wherein the second stationary link is fixed to the first movable link such that the second movable link is movable in the plane containing the axis line, and wherein the second movable link supports the sensor; a first biasing device which is associated with the first link device and which produces a thrust having a directional component resisting a load applied to the first movable link; and a second biasing device which is associated with the second link device and which produces a thrust having a directional component resisting a load applied to the second movable link.

In the sensor holding apparatus in accordance with the first mode of the present invention, the first link device is supported by the rotatable member rotatable relative to the base member about the vertical axis line, and the sensor is supported by the second movable link of the second link device supported by the first movable link of the first link device. Thus, the sensor can be easily moved to any position in a three-dimensional space. In addition, the first biasing device produces the thrust having the directional component resisting the load applied to the first movable link, and the second biasing device produces the thrust having the directional component resisting the load applied to the second movable link. Since the sensor supported by the second movable link is the load applied to the same, the load is largely reduced and accordingly the sensor can be held such that the sensor touches, i.e., lightly contacts the object. Therefore, the present sensor holding apparatus can hold the sensor such that the sensor touches the object, and can permit the sensor to be easily moved on the object to seek a target portion thereof to be sensed.

According to a second mode of the present invention, there is provided an apparatus for holding a sensor such that the sensor touches an object at an arbitrary position in a three-dimensional space, the apparatus comprising a base member; a movable member which is movable relative to the base member in a vertical direction; a load balancing device which applies, to the movable member, a thrust having a direction to cancel a load applied to the movable member; and a slide arm whose lengthwise dimension is changeable and which includes (a) a support end portion that supports the sensor and (b) a base end portion that is attached to an end portion of the movable member such that the base end portion is rotatable relative to the base member about a vertical axis line.

The sensor holding apparatus in accordance with the second mode of the present invention includes the movable member that is movable relative to the base member in the vertical direction; the load balancing device that applies, to the movable member, the thrust having the direction to cancel the load applied to the movable member; and the slide arm whose lengthwise dimension is changeable and which includes (a) the support end portion that supports the sensor and (b) the base end portion that is attached to the end portion of the movable member such that the base end portion is rotatable relative to the base member about the vertical axis line. Thus, the sensor can be easily moved to any position in a three-dimensional space. In addition, the load balancing device applies, to the movable member, the thrust having the direction to cancel the load applied to the movable member.

Since the sensor supported by the support end portion of the slide arm is the load applied to the movable arm, the load is largely reduced and accordingly the sensor can be held such that the sensor touches, i.e., lightly contacts the object. Therefore, the present sensor holding apparatus can hold the sensor such that the sensor touches the object, and can permit the sensor to be easily moved on the object to seek a target portion thereof to be sensed.

According to a third mode of the present invention, there is provided an apparatus for holding a sensor such that the sensor touches an object at an arbitrary position in a three-dimensional space, the apparatus comprising a base member; a slide arm whose lengthwise dimension is changeable and which includes (a) a base-end arm portion that is attached to the base member such that the base-end arm portion is rotatable relative to the base member about a vertical axis line and (b) a support-end arm portion that is attached to the base-end arm portion such that the support-end arm portion is movable relative to the base-end arm portion in a lengthwise direction of the slide arm; a link device including two pivotable links, and a stationary link and a movable link which are pivotably connected to opposite end portions of one of the two pivotable links and opposite end portions of an other of the two pivotable links, such that the two pivotable links, the stationary link, and the movable link cooperate with each other to define a quadrilateral, wherein the stationary link is attached to the support-end arm portion such that the movable link is movable in a plane containing the axis line, and wherein the movable link supports the sensor; and a biasing device which is associated with the link device and which produces a thrust having a directional component resisting a load applied to the movable link.

The sensor holding apparatus in accordance with the third mode of the present invention includes the slide arm whose lengthwise dimension is changeable and which includes (a) the base-end arm portion that is attached to the base member such that the base-end arm portion is rotatable relative to the base member about the vertical axis line and (b) the support-end arm portion that is attached to the base-end arm portion such that the support-end arm portion is movable relative to the base-end arm portion in the lengthwise direction of the slide arm; the link device including the two pivotable links, and the stationary link and the movable link that are pivotably connected to opposite end portions of one of the two pivotable links, respectively, and opposite end portions of an other of the two pivotable links, respectively, such that the two pivotable links, the stationary link, and the movable link cooperate with each other to define a quadrilateral, wherein the stationary link is attached to the support-end arm portion such that the movable link is movable in the plane containing the axis line, and wherein the movable link supports the sensor; and the biasing device that is associated with the link device and that produces the thrust having the directional component resisting the load applied to the movable link. Thus, the sensor can be easily moved to any position in a three-dimensional space. In addition, the biasing device applies, to the movable link, the thrust having the direction to cancel the load applied to the movable link. Since the sensor attached to the movable link is the load applied to the movable link, the load is largely reduced and accordingly the sensor can be held such that the sensor touches, i.e., lightly contacts the object. Therefore, the present sensor holding apparatus can hold the sensor such that the sensor touches the object, and can permit the sensor to be easily moved on the object to seek a target portion thereof to be sensed.

According to a fourth mode of the present invention, the sensor holding apparatus further comprises a universal joint which connects the sensor to the second movable link of the second link device, the support end portion of the slide arm, or the movable link of the link device.

In the sensor holding apparatus in accordance with the fourth mode of the present invention, the sensor is connected, via the universal joint, to the second movable link of the second link device, the support end portion of the slide arm, or the movable link of the link device. Thus, a degree of freedom of a posture that can be taken by the sensor relative to an outer surface of the object, such as a surface of a skin of a living being, can be increased.

According to a fifth mode of the present invention, the apparatus further comprises a stopper device which includes an operable member and which inhibits, when the operable member is not operated, a rotation of the universal joint, and permits, when the operable member is operated, the rotation of the universal joint.

The sensor holding apparatus in accordance with the fifth mode of the present invention includes the stopper device that inhibits, when the operable member is not operated, i.e., not in use, the rotation of the universal joint, and permits, when the operable member is operated or used by an operator, the rotation of the universal joint. Thus, the posture of the sensor relative to the outer surface of the object can be easily changed by operating the operable member, and the optimum posture of the sensor can be maintained by not operating the operable member.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
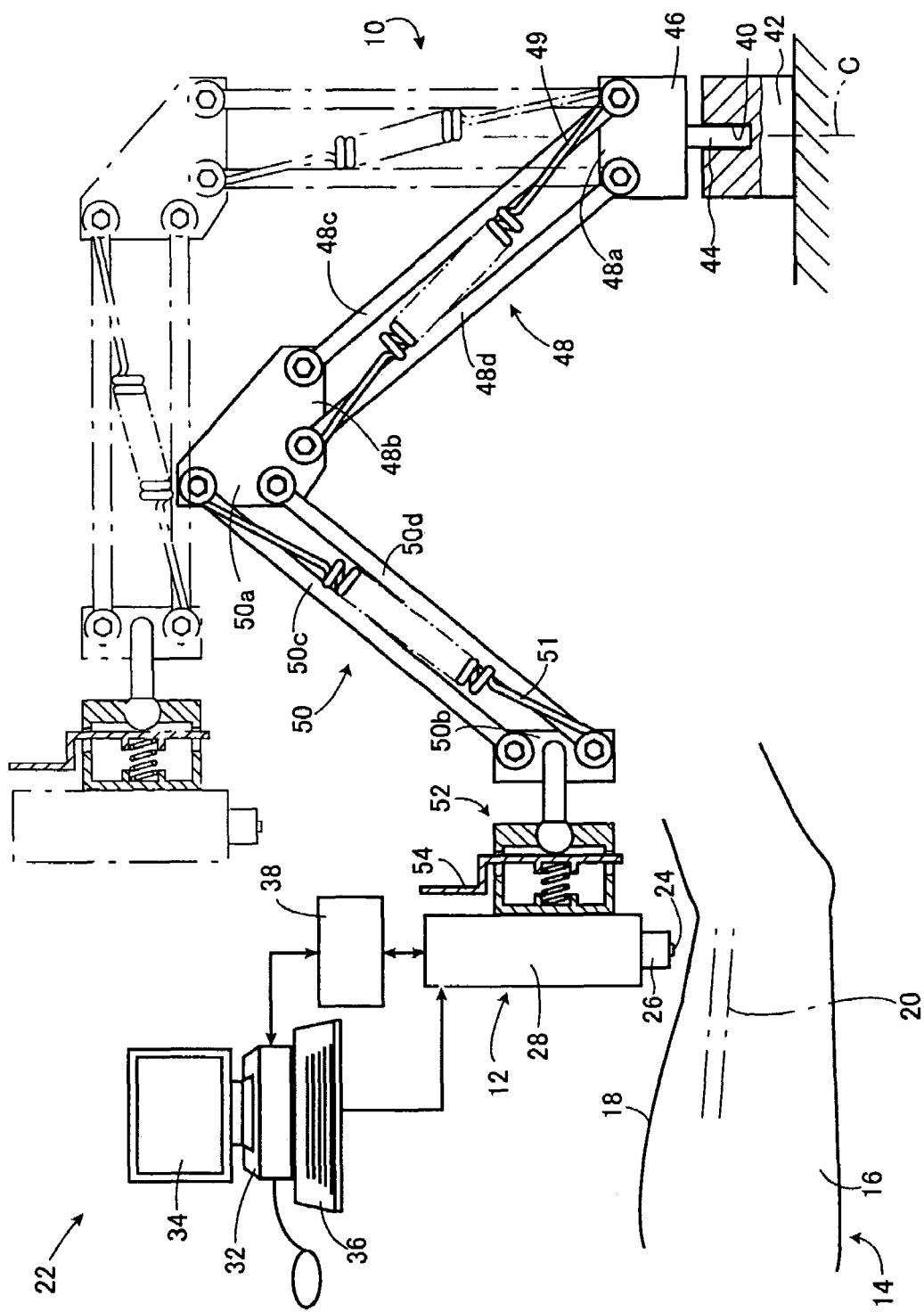
FIG. 1 is a schematic view of a blood-vessel-image measuring apparatus including a sensor holding apparatus as a first embodiment of the present invention.

Hereinafter, there will be described preferred embodiments of the present invention in detail by reference to the drawings. FIG. 1 is a front view for explaining a blood-vessel-image measuring apparatus 22 which includes an ultrasonic probe 12 as a sensor; and a sensor holding apparatus 10 as an embodiment of the present invention that holds the ultrasonic probe 12, and which measures, using the ultrasonic probe 12 held on a surface of a skin 18 of an upper arm 16 of a living being 14 (e.g., a living person) as an object, a transverse-cross-section image (i.e., a short-axis image) and/or a longitudinal-cross-section image (i.e., a long-axis image) of a blood vessel (e.g., an artery) 20 present right below the skin surface 18.

The ultrasonic probe 12 functions as a sensor that detects physical information of a living being, and includes a free-end portion 24 including a large number of ultrasonic transducers each of which is constituted by, e.g., a piezoelectric ceramics and which are arranged in one array (or two parallel arrays), i.e., are provided in the form of "an ultrasonic array (or arrays)"; a three-axis driving or positioning device 26; and a main frame 28.

The blood-vessel-image measuring apparatus 22 further includes an electronic control device 32 that is constituted by a so-called microcomputer; a monitor-image displaying device 34; a keyboard 36; and an ultrasonic-wave control circuit 38. The electronic control device 32 controls the ultrasonic-wave control circuit 38 to supply drive signals to the ultrasonic array at the free-end portion 24 of the ultrasonic probe 12, so that the ultrasonic array generates ultrasonic waves, receives the ultrasonic waves reflected from a tissue present under the skin surface 18, and produces reflected-ultrasonic-wave signals. The control device 32 receives the reflected-ultrasonic-wave signals from the ultrasonic array, processes the thus received signals, produces an ultrasonic image of the tissue under the skin surface 18, and controls the monitor-image displaying device 34 to display the thus produced ultrasonic image. More specifically described, when the control device 32 produces the transverse-cross-section image (i.e., the short-axis image) of the blood vessel 20, the control device 32 controls the three-axis positioning device 26 to position the ultrasonic array of the free-end portion 24 relative to the blood vessel 20 such that the ultrasonic array extends in a direction perpendicular to the blood vessel 20; and when the control device 32 produces the longitudinal-cross-section image (i.e., the long-axis image) of the blood vessel 20, the control device 32 controls the three-axis positioning device 26 to position the ultrasonic array relative to the blood vessel 20 such that the ultrasonic array extends in a direction parallel to the blood vessel 20.

The ultrasonic-wave control circuit 38 carries out, according to a command supplied from the electronic control device 32, a beam-forming operation in which a predetermined number of transducers (e.g., 15 transducers) starting with one of opposite ends of the ultrasonic array are simultaneously driven such that each of the transducers generates an ultrasonic wave having a frequency of about 10 MHz with a predetermined phase difference from the phase of the ultrasonic wave generated by each of the two transducers located adjacent the each transducer on either side of the same. While the predetermined number of transducers are shifted one transducer by one in a direction from the above-indicated one end of the ultrasonic array to the other end thereof, the ultrasonic array sequentially generates, toward the blood vessel 20, respective ultrasonic beams each of which is convergent with respect to the direction of extension of the ultrasonic array. Each time the ultrasonic array generates the ultrasonic beam, it receives the ultrasonic beam reflected from the blood vessel 20, and inputs a signal representing the received, reflected ultrasonic beam, to the control device 32. An outer surface of the free-end portion 24 in which the ultrasonic array is provided is covered with an acoustic lens 92 that causes the ultrasonic beams to converge with respect to a direction perpendicular to the direction of extension of the ultrasonic array.

The electronic control device 32 synthesizes or produces, based on the signals representing the reflected ultrasonic beams, a transverse-cross-section image (i.e., a short-axis image) of the blood vessel 20 present under the skin surface 18, and/or a longitudinal-cross-section image (i.e., a long-axis image) of the blood vessel 20, and controls the monitor-image displaying device 34 to display the thus produced image(s) of the blood vessel 20. In addition, the control device 32 calculates, from the produced image(s) of the blood vessel 20, a diameter of the same 20, i.e., a diameter of an endothelium (i.e., an inner layer (tunica intima)) of the same 20. Moreover, for the purpose of evaluating a function of the endothelium of the blood vessel 20, the control device 32 calculates a rate of change (%) [$=100\times(d_{max}-d)/d$, where d is a diameter of the vessel 20 when the living being 14 is at rest; and $d_{max}$ is a maximum diameter of the vessel 20 after the flow of blood is resumed] of the diameter of the vessel 20 that represents FMD (flow-mediated dilation) following postischemia reactive hyperemia.

The ultrasonic probe 12 is held by the sensor holding apparatus 10, such that the probe 12 takes a desirable posture and touches, at a desirable or predetermined position in a three-dimensional space, the skin surface 18 of the upper arm 16 of the living being 14 as the object, without changing a shape of the blood vessel 20 present right below the skin surface 18. Usually, a well-known coupling agent such as a jelly is interposed between the skin surface 18 and the outer surface of the free end portion 24 of the ultrasonic probe 12, for the purpose of preventing the attenuation of ultrasonic waves, or the reflection or scattering thereof at the interface of the two elements 18, 24, and thereby obtaining a clear ultrasonic image. The jelly may be a gel of a hydrophilic polymer that contains water at a high rate and has an intrinsic impedance [$=$(sound speed)$\times$(density)] sufficiently higher than that of air, and accordingly effectively restrains the attenuation of ultrasonic-wave signals transmitted or received. The jelly is, e.g., agar, but it may be replaced with a water bag, i.e., a water packed in a resin-based bag; olive oil; or glycerin.

The sensor holding apparatus 10 is fixed in position to a support member such as a desk or a seat. More specifically described, the sensor holding apparatus 10 includes a base member 42 having a fitting hole 40 extending along a vertical axis line, C; and a rotatable member 46 that has a fitting axis portion 44 that fits in the fitting hole 40 such that the axis portion 44 is rotatable relative thereto, so that the rotatable member 46 is rotatable about the vertical axis line C relative to the base member 42. The sensor holding apparatus 10 additionally includes a first link device 48 that is constituted by four links 48a, 48b, 48c, 48d including a horizontal, first stationary link 48a fixed to (i.e., integral with) the rotatable member 46; a second link device 50 that is constituted by four links 50a, 50b, 50c, 50d including a vertical, second stationary link 50a fixed to (i.e., integral with) an end portion of the first link device 48; a universal joint 52 that is fixed to an end portion of the second link device 50, connects the ultrasonic probe 12 to the same 50, and supports the probe 12 such that the probe 12 is universally rotatable; and a stopper device 56 (FIG. 2) that includes an operable lever 54 and that fixes the universal joint 52 while the lever 54 is not operated by an operator, and releases the fixation of the joint 52, i.e., permits the universal rotation of the joint 52 while the lever 54 is operated.

The first link device 48 includes the first stationary link 48a; a first movable link 48b extending parallel to the first stationary link 48a; and a pair of first pivotable links 48c, 48d which extend parallel to each other and each of which is pivotably connected, at two opposite ends thereof, to the first stationary link 48a and the first movable link 48b, respectively, so that the first stationary link 48a, the first movable link 48b, and the two first pivotable links 48c, 48d cooperate with each other to define a parallelogram. The first stationary link 48a is fixed to the rotatable member 46 such that the first movable link 48b is movable in a plane containing the vertical axis line C. In association with the first link device 48, there is provided a first coil spring 49 functioning as a first biasing device that produces a thrust having a directional component resisting a load applied to the first movable link 48b. The first coil spring 49 is connected at one end thereof to a connection point where one first pivotable link 48c and the first stationary link 48a are connected to each other, and is connected at the other end thereof to a connection point where the other first pivotable link 48d and the first movable link 48b are connected to each other, such that a moment produced by the first coil spring 49 in a direction to move the first movable link 48b upward, and a moment produced by the load applied to the first movable link 48b in a direction to move the same 48b downward are substantially cancelled by each other.

The second link device 50 includes a pair of second pivotable links 50c, 50d that extend parallel to each other; and the second stationary link 50a and a second movable link 50b which extend parallel to each other and each of which is pivotably connected, at two opposite ends thereof, to the two second pivotable links 50c, 50d, respectively, so that the second stationary link 50a, the second movable link 50b, and the two second pivotable links 50c, 50d cooperate with each other to define a parallelogram. The second stationary link 50a is fixed to the first movable link 48b such that the second stationary link 50a extends in a direction substantially perpendicular to the first stationary link 48a and such that the second movable link 50b is movable in the plane containing the vertical axis line C. In association with the second link device 50, there is provided a second coil spring 51 functioning as a second biasing device that produces a thrust having a directional component resisting a load applied to the second movable link 50b. The second coil spring 51 is connected at one end thereof to a connection point where one second pivotable link 50c and the second stationary link 50a are connected to each other, and is connected at the other end thereof to a connection point where the other second pivotable link 50d and the second movable link 50b are connected to each other, such that a moment produced by the second coil spring 51 in a direction to move the second movable link 50b upward, and a moment produced by the load applied to the second movable link 50b in a direction to move the same 50b downward are substantially cancelled by each other. Owing to the respective moment-canceling actions of the first and second coil springs 49, 51, the sensor holding apparatus 10 can hold the ultrasonic probe 12 such that the probe 12 is stopped at a desirable position, or is slowly moved downward, in the three-dimensional space, and such that the outer surface of the free end portion 24 of the probe 12 lightly touches the skin surface 18 without deforming the blood vessel 20 and closely contacts the same 18 via the coupling agent such as jelly, as indicated by solid lines in FIG. 1. In addition, the ultrasonic probe 12 can be moved upward as indicated by one-dot chain lines in FIG. 1.

Figure 2:
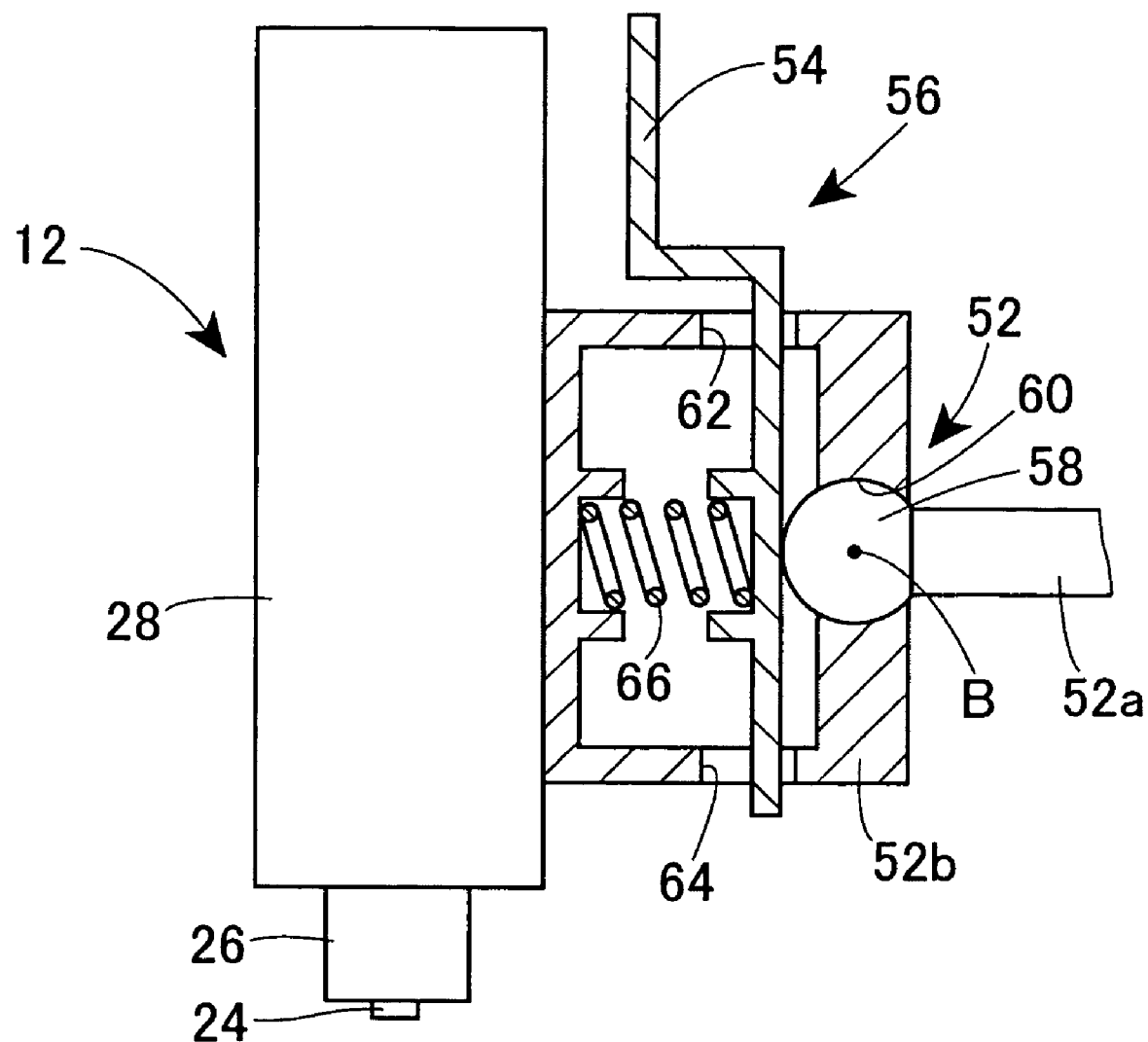
FIG. 2 is an enlarged view showing an end portion of the sensor holding apparatus of FIG. 1.

FIG. 2 is an enlarged view of the universal joint 52 and the stopper device 56. As shown in the figure, the universal joint 52 includes a first connection member 52a having a base end portion fixed to the second movable link 50b, and a free end portion 58 having a spherical shape; and a second connection member 52b that has a fitting hole 60 in which the spherical end portion 58 of the first connection member 52a slideably fits, and that is connected to the spherical end portion 58 such that the second connection member 52b is universally rotatable about a center, B, of the spherical portion 58. The second connection member 52b has two guide holes 62, 64 that cooperate with each other to guide the operable lever 54 of the stopper device 56 such that the operable lever 54 is movable toward, and away from, the spherical end portion 58 of the first connection member 52a.

The stopper device 56 includes, in addition to the operable lever 54, a pressing spring 66 that presses the operable lever 54 against the spherical end portion 58 of the first connection member 52a. In a usual state in which the operable lever 54 is not in use, the pressing spring 66 presses the operable lever 54 against the spherical portion 58, so as to inhibit the rotation of the universal joint 52 and thereby fix the same 52. However, when the operable lever 54 is used or operated by the operator against the biasing force of the pressing spring 66, and is moved away from the spherical portion 58, the fixation of the universal joint 52 is released and the universal rotation of the same 52 is permitted. Thus, the ultrasonic probe 12 can be moved to take a desirable posture.

As is apparent from the foregoing description of the sensor holding apparatus 10, the rotatable member 46 that is rotatable relative to the base member 42 about the vertical axis line C supports the first link device 48, the first movable link 48b of the first link device 48 supports the second link device 50, and the second movable link 50b of the second link device 50 supports the ultrasonic probe 12. Therefore, the ultrasonic probe 12 can be easily moved to any position in the three-dimensional space.

In addition, the first coil spring 49 as the first biasing device produces the thrust having the component in the direction against the load applied to the first movable link 48b; and the second coil spring 51 as the second biasing device produces the thrust having the component in the direction against the load applied to the second movable link 50b. Since the ultrasonic probe 12 is supported by the second movable link 50b, the load of the probe 12 can be largely reduced. Therefore, the ultrasonic probe 12 can be held by the sensor holding apparatus 10, in the state in which the probe 12 can lightly touch the living being 14 as the object, and the probe 12 can be easily moved on the skin surface 18 to find a target tissue of the subject 14.

In addition, in the sensor holding apparatus 10, the ultrasonic probe 12 as the sensor is connected to the second movable link 50b via the universal joint 52 that can be universally rotatable. Thus, a degree of freedom of the posture that can be taken by the probe 12 relative to the outer surface of the object, such as the skin surface 18 of the living being 14, can be increased.

In addition, the sensor holding apparatus 10 employs the stopper device 56 that inhibits the rotation of the universal joint 52 in the state in which the operable lever 54 as an operable member is not in use, and releases the fixation of the joint 52 when the lever 54 is operated by the operator. Therefore, when the operable lever 54 is operated, the posture of the ultrasonic probe 12 as the sensor can be easily changed relative to the skin surface 18 of the living being 14 as the outer surface of the object; and when the operable lever 54 is not in use, the optimum posture of the probe 12 can be maintained.

Next, there will be described other embodiments of the present invention. The same reference numerals as used in the first embodiment shown in FIGS. 1 and 2 are used to designate the corresponding elements or parts of the other embodiments, and the description thereof is omitted.

Figure 3:
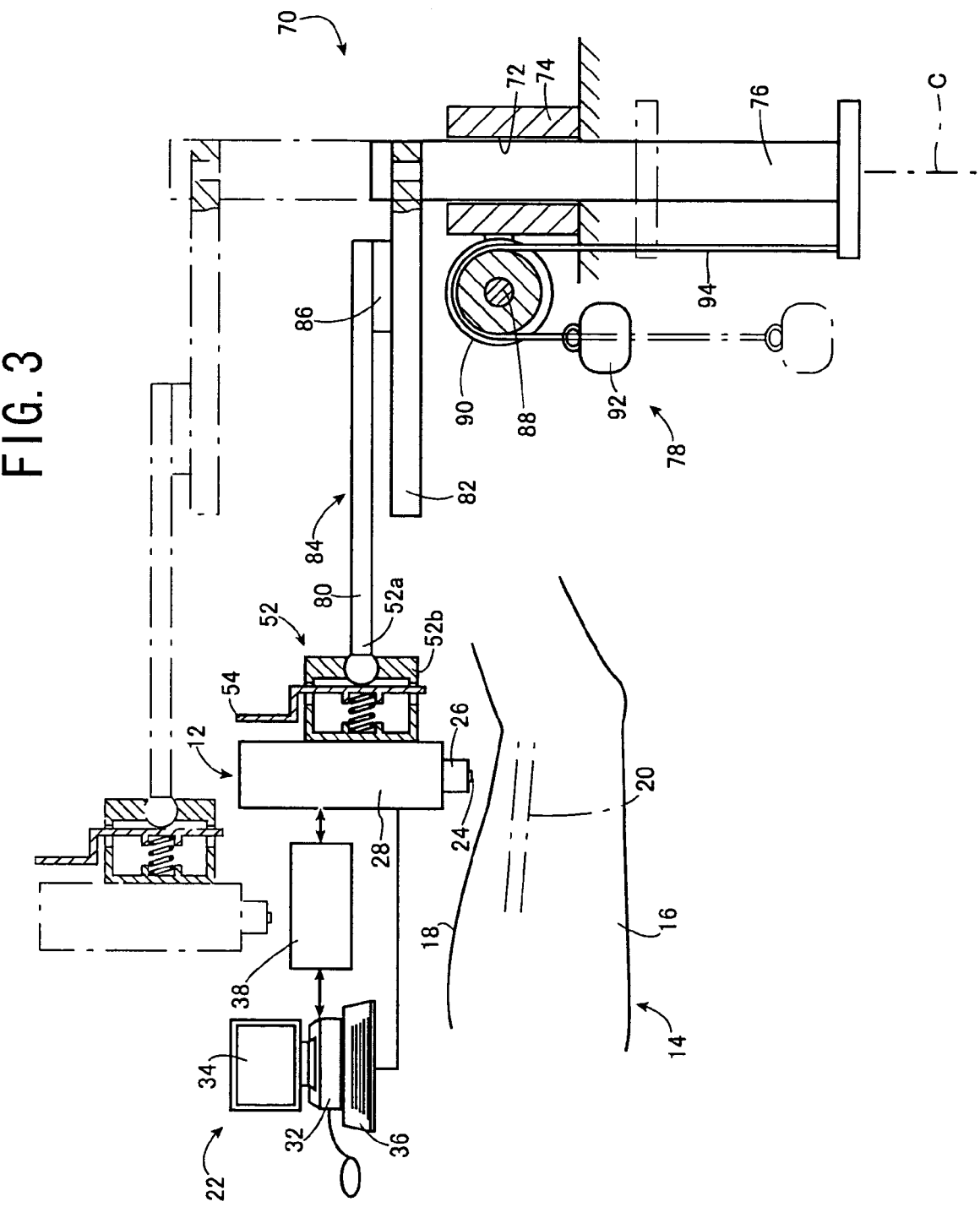
FIG. 3 is a schematic view corresponding to FIG. 1 and showing another blood-vessel-image measuring apparatus including another sensor holding apparatus as a second embodiment of the present invention.

FIG. 3 is a front view for explaining a blood-vessel-image measuring apparatus 22 which includes an ultrasonic probe 12 as a sensor; and a sensor holding apparatus 70 as a second embodiment of the present invention that holds the ultrasonic probe 12, and which measures, using the ultrasonic probe 12 held on a surface of a skin 18 of an upper arm 16 of a living being 14 (e.g., a living person) as an object, a transverse-cross-section image (i.e., a short-axis image) and/or a longitudinal-cross-section image (i.e., a long-axis image) of a blood vessel (e.g., an artery) 20 located right below the skin surface 18. The following description is focused on differences of the sensor holding apparatus 70 as the second embodiment from the sensor holding apparatus 10 as the first embodiment.

In the second embodiment, too, the ultrasonic probe 12 is held by the sensor holding apparatus 70, such that the probe 12 takes a desirable posture and touches, at a desirable or predetermined position in a three-dimensional space, the skin surface 18 of the upper arm 16 of the living being 14 as the object, without changing a shape of the blood vessel 20 located right below the skin surface 18.

The sensor holding apparatus 70 includes a base member 74 having a guide hole 72 extending along a vertical axis line, C; a movable member 76 that slideably fits in the guide hole 72 of the base member 74 and accordingly is movable relative to the same 74 in a vertical direction; a load balancing device 78 that applies, to the movable member 76, a thrust in a direction to cancel a load applied to the same 76; and a slide arm 84 whose length is changeable and which includes (a) a support arm portion 80 that supports the ultrasonic probe 12 via a universal joint 52 and a stopper device 56, and (b) a base arm portion 82 that is connected to an upper end of the movable member 76 such that the base arm portion 82 is rotatable relative to the base member 74 about the vertical axis line C.

The slide arm 84 additionally includes a slide device 86 that is provided in a base end portion of the support arm portion 80 and that allows the support arm portion 80 to be moved with an appropriate resistance in a lengthwise direction of the base arm portion 82. Thus, the total length of the slide arm 84 is changeable.

The load balancing device 78 includes a support axis member 88 that is fixed in position; a pulley 90 that is rotatably supported by the axis member 88; a cable 94 that is wound on the pulley 90 and is connected, at one of opposite ends thereof, to a lower end of the movable member 76; and a weight 92 that is connected to the other end of the cable 90. A load of the weight 92 is pre-set at a value substantially equal to a sum of respective loads of the movable member 76, the slide arm 84, the ultrasonic probe 12, the universal joint 52, and the stopper device 56. Thus, the support arm portion 80 of the slide arm 84, i.e., the sensor holding apparatus 70 can hold the ultrasonic probe 12 such that the probe 12 is stopped at a desirable position, or is slowly moved downward, in the three-dimensional space, and such that an outer surface of a free end portion 24 of the probe 12 lightly touches the skin surface 18 without deforming the blood vessel 20 and closely contacts the same 18 via a coupling agent such as jelly, as indicated by solid lines in FIG. 3. In addition, the ultrasonic probe 12 supported by the slide arm 84 can be moved upward as indicated by one-dot chain lines in FIG. 3.

Thus, the sensor holding apparatus 70 includes the movable member 76 that is movable relative to the base member 74 in the vertical direction; the load balancing device 78 that applies, to the movable member 76, the thrust in the direction to cancel the load applied to the same 76; and the slide arm 84 whose lengthwise dimension is changeable and which includes (a) the support arm portion 80 that supports the ultrasonic probe 12 and (b) the base arm portion 82 that is connected to the upper end of the movable member 76 such that the base arm portion 82 is rotatable relative to the base member 74 about the vertical axis line C. Therefore, the ultrasonic probe 12 can easily be moved to any position in the three-dimensional space. In addition, since the load balancing device 78 applies, to the movable member 76, the thrust in the direction to cancel the load applied to the same 76, the load of the ultrasonic probe 12 attached to the support arm portion 80 of the slide arm 84 can be largely reduced. Therefore, the ultrasonic probe 12 can be held by the sensor holding apparatus 70, in the state in which the probe 12 can lightly touch the living being 14 as the object, and the probe 12 can be easily moved on the skin surface 18 to find a target tissue of the living being 14.

In the sensor holding apparatus 70, the ultrasonic probe 12 as the sensor is connected to the slide arm 84 via the universal joint 52 that can be universally rotatable. Thus, a degree of freedom of the posture that can be taken by the probe 12 relative to the outer surface of the object, such as the skin surface 18 of the living being 14, can be increased.

In addition, the sensor holding apparatus 70 employs the stopper device 56 that inhibits the rotation of the universal joint 52 in the state in which the operable lever 54 as an operable member is not in use, and releases the fixation of the joint 52 when the lever 54 is operated by the operator. Therefore, when the operable lever 54 is operated, the posture of the ultrasonic probe 12 as the sensor can be easily changed relative to the skin surface 18 of the living being 14 as the outer surface of the object; and when the lever 54 is not in use, the optimum posture of the probe 12 can be maintained.

Figure 4:
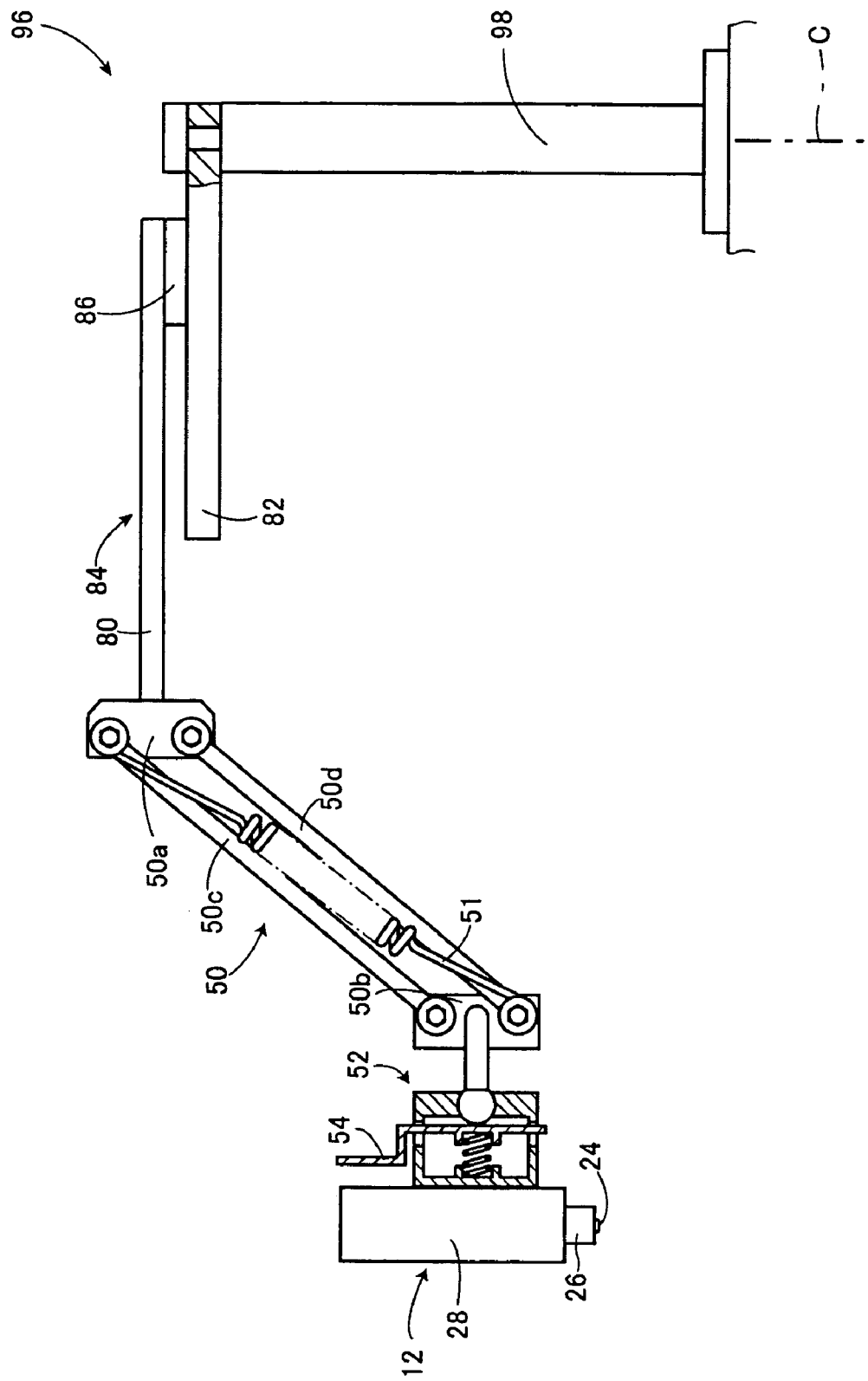
FIG. 4 is a schematic view corresponding to FIG. 1 and showing another blood-vessel-image measuring apparatus including another sensor holding apparatus as a third embodiment of the present invention.

FIG. 4 shows another sensor holding apparatus 96 as a third embodiment of the present invention that holds an ultrasonic probe 12 as a sensor. The sensor holding apparatus 96 includes a columnar base member 98 that is fixed in position and extends along a vertical axis line, C; a slide arm 84 whose lengthwise dimension is changeable and which includes (a) a support arm portion 80 and (b) a base arm portion 82 that is connected to an upper end of the base member 98 such that the base arm portion 82 is rotatable relative to the base member 98 about the vertical axis line C; and a link device 50 including a stationary link 50a fixed to the support arm portion 80 of the slide arm 84.

More specifically described, the slide arm 84 additionally includes a slide device 86 that allows the support arm portion 80 to be moved with an appropriate resistance in a lengthwise direction of the base arm portion 82. Thus, the lengthwise dimension of the slide arm 84 is changeable. The link device 50 is identical with the second link device 50 shown in FIG. 1, and includes a pair of pivotable links 50c, 50d that extend parallel to each other; and the stationary link 50a and a movable link 50b which extend parallel to each other and each of which is pivotably connected, at two opposite ends thereof, to the two pivotable links 50c, 50d, respectively, so that the stationary link 50a, the movable link 50b, and the two pivotable links 50c, 50d cooperate with each other to define a parallelogram. The stationary link 50a is fixed to the support arm portion 80 such that the movable link 50b is movable in a plane containing the vertical axis line C, and the movable link 50b supports the ultrasonic probe 12 via a universal joint 52 and a stopper device 56. In association with the link device 50, there is provided a coil spring 51 functioning as a biasing device that produces a thrust having a component in a direction against a load applied to the movable link 50b. Thus, the ultrasonic probe 12 can easily be moved to any position in a three-dimensional space. Since the coil spring 51 applies, to the movable link 50b, the thrust in the direction to cancel the load applied to the movable link 50b, the load of the ultrasonic probe 12 attached to the movable link 50b can largely be reduced. Therefore, the ultrasonic probe 12 can be held by the sensor holding apparatus 96, in the state in which the probe 12 can lightly touch the living being 14 as the object, and the probe 12 can easily be moved on the skin surface 18 to find a target tissue of the living being 14.

While the present invention has been described in its preferred embodiments by reference to the drawings, it is to be understood that the invention may otherwise be embodied.

For example, in the sensor holding apparatus 10 shown in FIG. 1 or the sensor holding apparatus 96 shown in FIG. 4, each of the first and second coil springs 49, 50, or the coil spring 50 may be replaced with an elastic body or member such as a synthetic rubber, or an air cylinder having an air chamber that accommodates an air having a negative pressure.

In addition, in each of the sensor holding apparatuses 10, 70, 96, the universal joint 52 is used to support the ultrasonic probe 12. However, the universal joint 52 may be omitted.

In addition, in each of the sensor holding apparatuses 10, 70, 96, the stopper device 56 is used to inhibit the rotation of the universal joint 52. However, the stopper device 56 may be omitted in the case where the universal joint 52 is rotated with an appropriate resistance.

In addition, in each of the sensor holding apparatuses 70, 96, the slide arm 84 has a double structure in which the support arm portion 80 is movable in the lengthwise direction of the base arm portion 82. However, the slide arm 84 may have a triple structure including three arm portions that are movable relative to each other.

In addition, in the sensor holding apparatus 70 shown in FIG. 3, the slide arm 84 is rotatable relative to the movable member 76 about the vertical axis line C. However, the slide arm 84 may be fixed to the movable member 76, and the movable member 76 may be rotatable about the vertical axis line C.

In addition, in each of the sensor holding apparatuses 10, 70, 96, the ultrasonic probe 12 is so held as to tough the skin surface 18 of the living being 14. However, the probe 12 may be so held as to tough an internal object present in the living being 14, such as an organ.

In addition, in each of the sensor holding apparatuses 10, 70, 96, the base member 42, 74, 98 may be modified in various manners with respect to, e.g., its height dimension and/or its shape.

The present invention may be embodied with various changes and improvements that may occur to a person skilled in the art, without departing from the scope and spirit of the invention.

What is claimed is:

1. An apparatus for holding a sensor such that the sensor touches an object at an arbitrary position in a three-dimensional space, the apparatus comprising:
   a base member;
   a rotatable member which is rotatable relative to the base member about a vertical axis line;
   a first link device including a first stationary link, a first movable link, and two first pivotable links which are pivotably connected to opposite end portions of the first stationary link and opposite end portions of the first movable link, such that the first stationary link, the first movable link, and the two first pivotable links cooperate with each other to define a quadrilateral, wherein the first stationary link is fixed to the rotatable member such that the first movable link is movable in a plane containing the axis line;
   a second link device including two second pivotable links, and a second stationary link and a second movable link which are pivotably connected to opposite end portions of one of the two second pivotable links and opposite end portions of an other of the two second pivotable links, such that the two second pivotable links, the second stationary link, and the second movable link cooperate with each other to define a quadrilateral, wherein the second stationary link is fixed to the first movable link such that the second movable link is movable in the plane containing the axis line, and wherein the second movable link supports the sensor;
   a first biasing device which is associated with the first link device and which produces a thrust having a directional component resisting a load applied to the first movable link; and
   a second biasing device which is associated with the second link device and which produces a thrust having a directional component resisting a load applied to the second movable link.

2. The apparatus according to claim 1, further comprising a universal joint which connects the sensor to the second movable link of the second link device.

3. The apparatus according to claim 2, further comprising a stopper device which includes an operable member and which inhibits, when the operable member is not operated, a rotation of the universal joint, and permits, when the operable member is operated, the rotation of the universal joint.

4. An apparatus for holding a sensor such that the sensor touches an object at an arbitrary position in a three-dimensional space, the apparatus comprising:
   a base member;
   a movable member which is movable relative to the base member in a vertical direction;
   a load balancing device which applies, to the movable member, a thrust having a direction to cancel a load applied to the movable member; and
   a slide arm whose lengthwise dimension is changeable and which includes (a) a support end portion that supports the sensor and (b) a base end portion that is attached to an end portion of the movable member such that the base end portion is rotatable relative to the base member about a vertical axis line.

5. The apparatus according to claim 4, further comprising a universal joint which connects the sensor to the support end portion of the slide arm.

6. The apparatus according to claim 5, further comprising a stopper device which includes an operable member and which inhibits, when the operable member is not operated, a rotation of the universal joint, and permits, when the operable member is operated, the rotation of the universal joint.

7. An apparatus for holding a sensor such that the sensor touches an object at an arbitrary position in a three-dimensional space, the apparatus comprising:
   a base member;
   a slide arm whose lengthwise dimension is changeable and which includes (a) a base-end arm portion that is attached to the base member such that the base-end arm portion is rotatable relative to the base member about a vertical axis line and (b) a support-end arm portion that is attached to the base-end arm portion such that the support-end arm portion is movable relative to the base-end arm portion in a lengthwise direction of the slide arm;
   a link device including two pivotable links, and a stationary link and a movable link which are pivotably connected to opposite end portions of one of the two pivotable links and opposite end portions of an other of the two pivotable links, such that the two pivotable links, the stationary link, and the movable link cooperate with each other to define a quadrilateral, wherein the stationary link is attached to the support-end arm portion such that the movable link is movable in a plane containing the axis line, and wherein the movable link supports the sensor; and a biasing device which is associated with the link device and which produces a thrust having a directional component resisting a load applied to the movable link.

8. The apparatus according to claim 7, further comprising a universal joint which connects the sensor to the movable link of the link device.

9. The apparatus according to claim 8, further comprising a stopper device which includes an operable member and which inhibits, when the operable member is not operated, a rotation of the universal joint, and permits, when the operable member is operated, the rotation of the universal joint.

* * * * *